United States Patent [19]

Korbin

[11] 4,071,320
[45] Jan. 31, 1978

[54] DEVICE FOR THE QUANTITATIVE DETERMINATION OF IMPURITIES, ESPECIALLY BACTERIA, ON FLAT SURFACES

[76] Inventor: Martin Korbin, An der Eisenbahn 1a, 6392 Neu Anspach 1, Germany

[21] Appl. No.: 787,387

[22] Filed: Apr. 14, 1977

[30] Foreign Application Priority Data

Apr. 27, 1976 Germany ............................ 2618334

[51] Int. Cl.$^2$ ...................... C12B 1/04; G01N 1/02; G01N 13/00
[52] U.S. Cl. ...................................... 23/259; 23/292; 195/127; 195/139
[58] Field of Search .............. 23/259, 23/292, 230 B; 195/139

[56] References Cited

U.S. PATENT DOCUMENTS

| | | | |
|---|---|---|---|
| 3,694,320 | 9/1972 | Buissiere | 23/292 X |
| 3,751,341 | 8/1973 | Seitz | 195/139 |
| 3,813,223 | 5/1974 | Fleck | 23/259 |
| 3,846,077 | 11/1974 | Ohringer | 23/259 |
| 3,876,378 | 4/1975 | Montagnon | 23/259 X |
| 3,955,423 | 5/1976 | Ohringer | 23/230 B X |
| 4,007,012 | 2/1977 | Greenwald | 23/292 X |
| 4,014,322 | 3/1977 | Shah | 23/292 X |
| 4,022,576 | 5/1977 | Parker | 23/292 X |

*Primary Examiner*—Sidney Marantz

*Attorney, Agent, or Firm*—Friedman, Goodman & Teitelbaum

[57] ABSTRACT

A device for quantitative determination of impurities, especially bacteria, on a flat surface including a body member provided with a centrally located cylindrical rinsing chamber and an annular suction chamber surrounding the rinsing chamber, whereby the suction chamber generates a subpressure therein to press the rinsing chamber against the flat surface being investigated. The rinsing chamber has an opening adapted to be placed on the flat surface, and at least one aperture, preferably two apertures, spaced from the opening for connecting the rinsing chamber with the outside atmosphere for permitting both liquid passage and air passage from outside the body member into the rinsing chamber and vice versa. An outer sealing edge is provided around the suction chamber and an inner sealing edge is disposed on a common wall between the rinsing chamber and the sealing chamber for providing a liquid-tight and an air-tight seal therebetween to maintain the subpressure within the suction chamber. An edge portion of the body member overlaps the suction chamber and tapers from a thick cross section to a thin cross section in a direction towards the outer sealing edge for flexibility thereof. Preferably, the body member is a one piece construction which is fabricated from a flexible material, preferably rubber. One of the apertures is adapted to receive a liquid conveying arrangement such as a suction siphon, insertable therein for the liquid passage thereof into and out of the rinsing chamber.

10 Claims, 2 Drawing Figures

DEVICE FOR THE QUANTITATIVE DETERMINATION OF IMPURITIES, ESPECIALLY BACTERIA, ON FLAT SURFACES

The invention relates to a device for the quantitative determination of impurities, especially bacteria, on flat surfaces.

In the pharmaceutical, cosmetic and food industry, but also in large kitchens, hotels, in the household, and especially in hospitals, it is necessary to check the surrounding working surfaces, floors and walls at regular intervals for harmful contaminations or impurities, especially bacterial contaminations, so that the pure or clean quality of the products to be produced is assured so that a harmful impairment of the human organism, for example through infections, is avoided. Pharmaceutical and cosmetic products, as well as foods, must be germ free. In large kitchens, hotels, in the houshold and especially in hospitals, inadmissible contaminations can be extremely grave sources of disease and infection. In this context the quantitative determination of the contamination density, especially bacterial density, is an important requirement.

The quantitative determination of surface contaminations, especially contaminations by bacteria, was hitherto accomplished, for example, by a process whereby on the surface to be investigated, there was laid a small (sterile) metal frame and the surface bounded by the frame was rubbed off with a (sterile) batting carrier. The contamination absorbed by the batting (wadding) carrier was then fed to a suitable solvent. In the case of the determination of the bacteria density, for example, it was fed to a suitable solid or liquid nutrient substrate. This rubbing off process was repeated until it was believed that the entire contamination in the bounded surface area was rubbed off. This process is extremely time-consuming and does not offer the assurance of an accurate quantitative determination (see Zbl.Bakt.Hyg. 1st dept., Orig. B 159 (1974), page 292).

In the so-called "indirect impress technique" (Abklatschtechnik) (cf. E. Kanz, Hospitalismus-Fibel, 2nd ed., W. Kohlhammer, Stuttgart, Berlin, Cologne, Mainz (1966), pages 14 and 15), a cellophane foil soaked with sterile physiological common salt solution is pressed on the area to be investigated. After its removal, the foil is laid, for the purpose of germ-number determination, on a suitable nutrient substrate and then incubated. There is then seen on the solid nutrient substrate, a mirror-image topographic reproduction of the impressed surface. In this "direct impress method", by impressing a nutrient substrate, there is established a direct contact with the area to be investigated. However, neither of the last two above mentioned methods assure an accurate quantitative determination of surface contaminations.

It is accordingly an object of the present invention to provide a device for the quantitative determination of impurities, especially bacteria, on flat surfaces which avoids the aforementioned problems of the prior art devices.

The object of the present invention, therefore, is to provide a device, which regardless of the degree and type of the contamination, for example, the type of bacteria, in a simple and rapid manner, without expensive special apparatus units and at low examination costs, permits an accurate quantitative determination of the density of contamination.

This above objective is solved according to the present invention by a rinsing chamber open to the area to be investigated, which has at least one opening allowing liquid passage and air passage from outside into the rinsing chamber and vice versa, and which is applicable to the area to be examined in a liquid-tight arrangement provided by a sealing edge thereon.

With the above and additional objects and advantages in view, as will hereinafter appear, this invention comprises the devices, combinations and arrangements of parts hereinafter described by way of example and illustrated in the accompanying drawings of a preferred embodiment in which.

Figure 1:
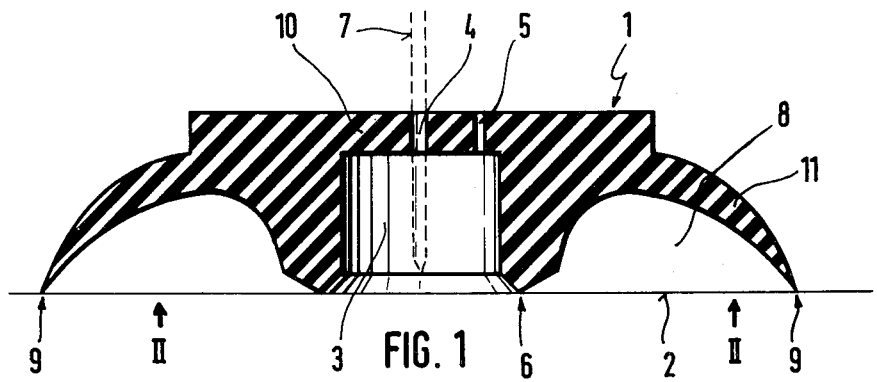
FIG. 1 shows schematically the device of the present invention in section.
Figure 2:
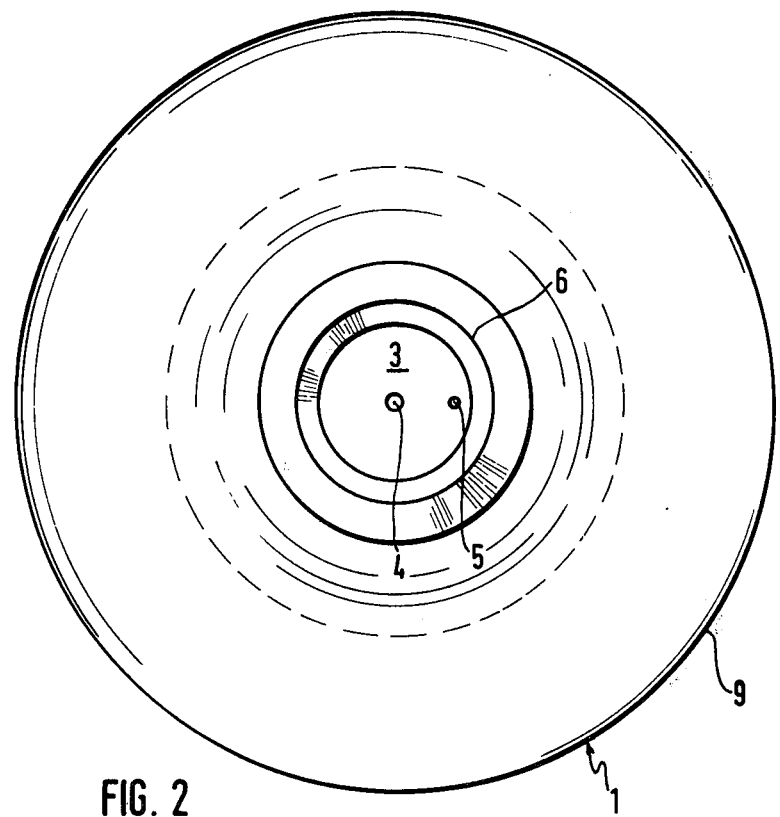
FIG. 2 shows a bottom view of the device from direction II of FIG. 1.

The process for the quantitative determination of the contamination is carried out with use of the device of the invention as follows:

The downward-open rinsing chamber is applied to the area to be investigated with its sealing edge in an air-tight relationship therewith. The sealing edge bounds an exactly defined surface area of the surface to be investigated. Then, through a passage opening in the device, there is introduced a liquid which removes or absorbs the contamination to be determined from the surface. In the determination of bacteria, there is used, for example, a physiological common salt solution, where in the determination of radioactive contaminations, there are used other suitable solutions. After the introduction of the liquid into the rinsing chamber the liquid is then drawn or sucked out. The process of introducing and sucking out is then repeated a number of times, until the entire surface contamination has been absorbed by the liquid. The liquid now contains the contamination, where the density is determined by usual chemical, physical or biochemical processes. In the determination of the bacteria density, the liquid containing the absorbed bacterial or corresponding constituents or dilutions thereof is placed on a nutrient substrate carrier. In the determination of radioactive contaminations, the liquid can be fed to a particle counter, for example, a scintillation counter.

Preferably two separate openings are provided, one for the liquid passage and the other for the air passage. In the liquid passage opening, there is provision made for the insertion of a liquid conveying arrangement, for example, a suction siphon. With the aid of the suction siphon, a defined amount of liquid can be introduced arbitrarily as many times as required into the rinsing chamber and again be drawn out, until the entire surface contamination has been absorbed by the liquid. Here it does not matter whether or not, in the last stroke of the suction siphon, the entire amount of liquid that was introduced into the rinsing chamber is again drawn out. A corresponding correction of the measuring result can be carried out if the volumes of liquid present in the siphon before the start of the rinsing process and after the start of the rinsing process are determined.

It is also possible, however, to provide a common opening in the rinsing chamber for both the liquid passage and the air passage, into which there is insertable a liquid conveying arrangement which allows the entry of liquid into the rinsing chamber and at the same time the escape of air from the rinsing chamber, and conversely. This can be realized, for example, by the one opening having a somewhat larger diameter than the outside diameter of the suction siphon which is inserted as the liquid conveying arrangement into the opening. While the liquid is passed from the suction siphon into the rinsing chamber, the air can escape to the outside through the interspace between liquid conveying capillary of the suction siphon and the opening edge, or the air can flow into the rinsing chamber through the interspace when the liquid is drawn out from the rinsing chamber by means of the suction siphon. There can also be used here, for example, a special suction siphon which besides the liquid capillary that is extendable to the surface being examined, also an air capillary which is extendable only into the passage opening of the rinsing chamber.

In order that the device of the present invention does not have to be constantly pressed, say by hand, against the surface being investigated to provide an air-tight or liquid-tight arrangement during the rinsing operation, the device of the present invention can also have two sealing edges to provide a suction chamber which is applied in an air-tight and liquid-tight relationshp to the surface to be investigated. Accordingly, a partial vacuum is generated in the suction chamber, so that the rinsing chamber is pressed in an air-tight and liquid-tight arrangement on the surface to be investigated. With the presence of this suction chamber which generates a partial vacuum therein, the entire device of the present invention, therefore, adheres to the area to be investigated as long as the partial vacuum is maintained.

In order not to generate the partial vacuum by drawing off air, for example, by means of a pump, at least one part of the suction chamber may include a flexible material, so that the subpressure in the suction chamber can be generated by pressing the device against the surface to be investigated. In the pressed-on state, the rinsing chamber is pressed into an air-tight and liquid-tight position, where the inner one of the sealing edges adjacent thereto is disposed against the surface to be investigated. During the pressing-on operation, in a manner similar to that used in a suction bell for plumbing clearance, the volume of the suction chamber is reduced a certain degree, whereby the air present in the suction chamber is pressed out. On completion of the pressing-on operation, the suction chamber spreads out somewhat by reason of the flexibility of the material used in at least the one part, whereby the partial vacuum is formed in it by the increased volume since the suction chamber adheres air-tight to the surface so that the expelled air cannot return to the increased volume.

In an especially simple construction of the present invention, the device is formed as a plate-shaped hood, in which the cylindrical rinsing chamber is disposed approximately in the central portion thereof and is surrounded by the approximately annular suction chamber. This construction has, besides the simple producibility thereof, the advantage that the somewhat more critical air-tight and liquid-tight inner sealing edge adjacent to the rinsing chamber is only relatively shorter in comparison to the air-tight and liquid-tight outer sealing edge of the suction chamber.

The passage openings for air and liquid are provided, in the interest of simplicity, preferably in the base member of the rinsing chamber. It is noted that the suction chamber should be disposed immediately adjacent to the rinsing chamber, so that the two chambers have a common air-tight and liquid-tight sealing edge provided by the inner sealing edge.

In order in all cases to assure an air-tight and liquid-tight engagement of the inner sealing edge separating the rinsing chamber and the suction chamber, and at least an air-tight engagement (though a liquid-tight engagement is also provided) of the outer sealing edge of the suction chamber, an edge portion of the device overlapping the suction chamber extends tapering toward the air-tight outer sealing edge and is axially extended somewhat further outwardly in the direction of the surface to be investigated than the inner sealing edge separating the rinsing chamber and the suction chamber. Thereby, it is taken into account that in the pressing of the suction chamber against the surface to be investigated and in generating a subpressure in the suction chamber, that the edge portion overlapping the suction chamber is bent back somewhat before the inner sealing edge separating the rinsing chamber and the suction chamber comes into engagement against the surface to be investigated. This construction assures the slight volume reduction of the suction chamber which is required for the generation of the subpressure in the suction chamber.

In an especially simple embodiment, the device of the present invention is made in one piece of flexible material, preferably rubber.

Referring now to the drawings, the device 1 according to the present invention for the quantitative determination of impurities, especially bacteria, on a substantially flat surface 2, is made in one piece of a flexible, autocaveable rubber (Shove harness ca. 40 degrees) and has substantially the form of a plate whose base is provided with a rinsing chamber of essentially cylindrical form open to the surface 2 in its operating position. In the base portion 10 of the rinsing chamber 3, there is provided a liquid passage opening 4 and a separate air passage opening 5. Into the liquid passage opening 4, there is insertable a conventional suction siphon 7 (represented in part and in broken lines). The rinsing chamber 3 is provided with an inner sealing edge 6 disposed adjacent thereto to provide a liquid-tight and air-tight seal with the surface 2. With the aid of the suction siphon 7, liquid for the dissolving and releasing of the contamination to be determined from the area bounded by the sealing edge 6 can be introduced through the liquid passage opening 4 into the rinsing chamber 3 and drawn out therefrom again, as set forth above. In the introduction or drawing out of the liquid, air can escape from the rinsing chamber 3 into the surrounding atmosphere or enter the rinsing chamber 3, preferably through the opening 5 or in any other manner set forth above.

An edge portion 11 of the plate-form device 1 overlaps a suction chamber 8, which is provided with an air-tight outer edge 9 when disposed on the surface 2, where the edge 9 also provides a liquid-tight seal. The edge portion 11 tapers from a thick cross section to a thin cross section toward the outer sealing edge 9. In the unpressed state of the device 1, as compared to the pressed-on state shown in FIG. 1, the outer sealing edge 9 extends further in the axial direction away from the base portion 10 (towards the surface 2) than the inner sealing edge 6. By means of the flexibility of the edge portion 11, the device 1 can be pressed in the manner of a suction cup against the surface 2 to provide the subpressure within the suction chamber 8, where the device 1 adheres automatically to the surface 2 and remains in this adhered condition during the entire rinsing process. When pressing the device 1 against the surface 2, therefore, the edge portion 11 with the outer sealing edge 9 yields somewhat, until the rinsing chamber 3 with the adjacent inner sealing edge 6 is disposed airtightly and liquid-tightly on the surface 2. The rinse-off process can then commence in a manner described above.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A device for quantitative determination of impurities, especially bacteria, on a flat surface, said device comprising a body member provided with a rinsing chamber having an opening adapted to be placed on the flat surface to be investigated in open communication therewith, aperture means spaced from said opening and connecting said rinsing chamber with the atmosphere outside said body member for permitting both liquid passage and air passage from outside said body member into said rinsing chamber and vice versa, and sealing means on said body member for providing a liquid-tight and an air-tight seal between said rinsing chamber and the flat surface being investigated.

2. A device according to claim 1, wherein said aperture means includes at least one aperture adapted to receive a liquid conveying arrangement insertable therein for the liquid passage thereof into and out of said rinsing chamber.

3. A device according to claim 2, wherein said aperture means includes a second aperture for the air passage thereof into and out of said rinsing chamber.

4. A device according to claim 3, wherein said one and second apertures are provided in a base portion of said body member opposite said opening of said rinsing chamber.

5. A device according to claim 1, wherein said body member is a one piece construction and is fabricated from a flexible material.

6. A device according to claim 1, wherein said body member includes a suction chamber to generate a subpressure therein, said suction chamber coacting with said sealing means to press said rinsing chamber against the flat surface being investigated in a liquid-tight and an air-tight relationship.

7. A device according to claim 6, wherein said suction chamber is at least partially fabricated from a flexible material to permit said body member to be pressed against the flat surface for generating said subpressure.

8. A device according to claim 6, wherein said suction chamber is disposed adjacent to said rinsing chamber, said sealing means including an inner sealing edge positioned between said suction chamber and said rinsing chamber to define a common wall therebetween.

9. A device according to claim 8, wherein said body member has a plate-shaped configuration, said rinsing chamber being cylindrically shaped and being centrally disposed in said body member, said suction chamber being approximately annular and surrounding said rinsing chamber, said sealing means including an outer sealing edge positioned around an outer wall of said suction chamber, said inner and outer sealing edges coacting together for maintaining said subpressure within said suction chamber.

10. A device according to claim 9, wherein an edge portion of said body member overlaps said suction chamber and tapers from a thick cross section to a thin cross section in a direction towards said outer sealing edge for flexibility thereof.

* * * * *